(12) United States Patent
Kimata et al.

(10) Patent No.: US 8,860,439 B2
(45) Date of Patent: Oct. 14, 2014

(54) METHOD AND DEVICE FOR DETECTING PARTICULATE MATTER CONTAINED IN A GAS TO BE MEASURED

(75) Inventors: Takehito Kimata, Kariya (JP); Mikiyasu Matsuoka, Obu (JP)

(73) Assignee: Denso Corporation, Kariya (JP)

( * ) Notice: Subject to any disclaimer, the term of this patent is extended or adjusted under 35 U.S.C. 154(b) by 325 days.

(21) Appl. No.: 13/283,885

(22) Filed: Oct. 28, 2011

(65) Prior Publication Data

US 2012/0103059 A1 May 3, 2012

(30) Foreign Application Priority Data

Oct. 28, 2010 (JP) .................. 2010-242162

(51) Int. Cl.
*G01R 27/26* (2006.01)
*G01N 15/06* (2006.01)
*F01N 11/00* (2006.01)
*G01N 27/62* (2006.01)
*F01N 9/00* (2006.01)

(52) U.S. Cl.
CPC ............. *G01N 15/0656* (2013.01); *Y02T 10/47* (2013.01); *F01N 9/002* (2013.01); *F01N 2550/04* (2013.01); *F01N 2560/05* (2013.01); *F01N 11/00* (2013.01)
USPC ........................................ 324/663; 324/464

(58) Field of Classification Search
CPC .................. G01N 15/0656; G01N 27/221

USPC ........ 324/71.4, 663, 464, 690, 696, 715–719, 324/724; 73/23.33; 204/406, 424
See application file for complete search history.

(56) References Cited

U.S. PATENT DOCUMENTS

| | | | | |
|---|---|---|---|---|
| 6,634,210 B1 * | 10/2003 | Bosch et al. | ................ | 73/23.33 |
| 7,069,770 B2 * | 7/2006 | Chen et al. | ................ | 73/31.05 |
| 7,609,068 B2 * | 10/2009 | Ripley | ........................ | 324/512 |
| 8,176,768 B2 * | 5/2012 | Kondo et al. | ............... | 73/23.33 |
| 2004/0217000 A1 * | 11/2004 | Yamamoto et al. | .......... | 204/424 |
| 2009/0217737 A1 * | 9/2009 | Dorfmueller et al. | ....... | 73/28.01 |
| 2010/0000404 A1 * | 1/2010 | Sakuma et al. | .................... | 95/3 |
| 2010/0000863 A1 * | 1/2010 | Kondo et al. | ............... | 204/406 |
| 2010/0229629 A1 * | 9/2010 | Egami et al. | ................ | 73/28.01 |

FOREIGN PATENT DOCUMENTS

| | | |
|---|---|---|
| JP | S59-197847 | 11/1984 |
| WO | WO 2008/031654 | 3/2008 |
| WO | WO 2008/138659 | 11/2008 |

\* cited by examiner

*Primary Examiner* — Huy Q Phan
*Assistant Examiner* — Raul Rios Russo
(74) *Attorney, Agent, or Firm* — Nixon & Vanderhye PC

(57) ABSTRACT

A particulate matter detection element includes a capacitance component disposed in parallel with a detected resistance $R_{SEN}$. A direct current-power source that supplies a direct current ($I_{DC}$) for particulate matter detection, and an alternating-current power source that supplies an alternating current ($I_{AC}$) for disconnection detection are provided.

9 Claims, 13 Drawing Sheets

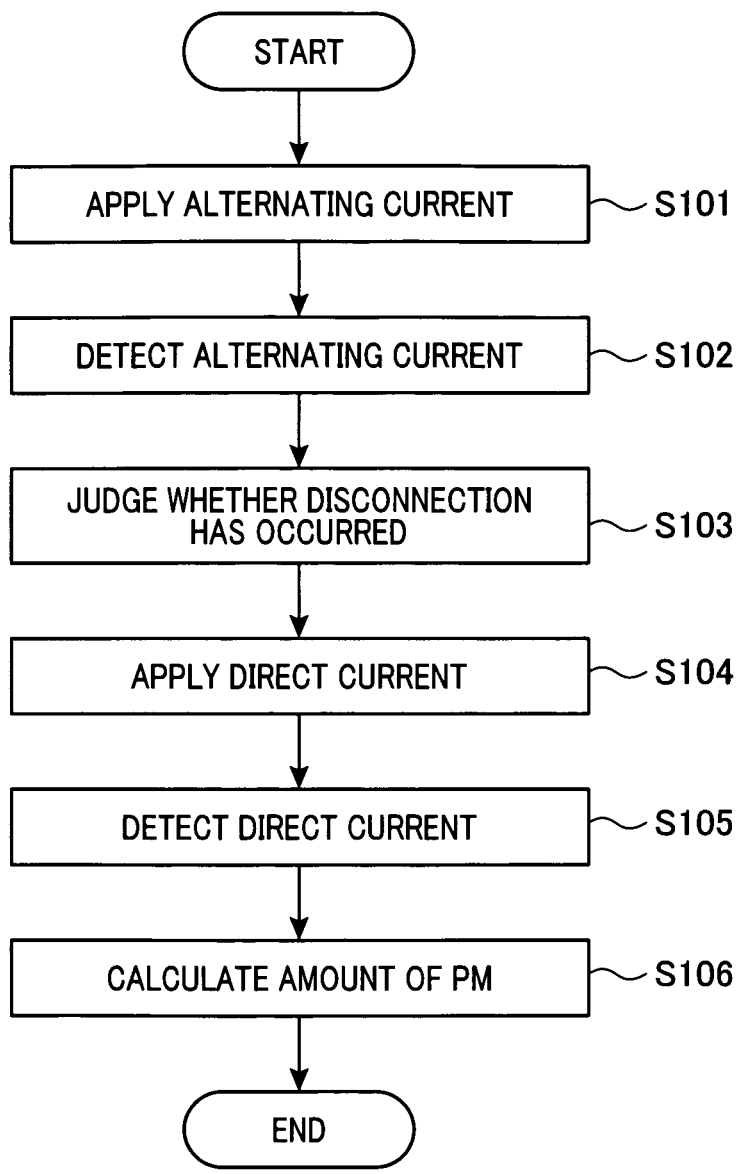

METHOD AND DEVICE FOR DETECTING PARTICULATE MATTER CONTAINED IN A GAS TO BE MEASURED

CROSS REFERENCE TO RELATED APPLICATION

This application is based upon and claims the benefit of priority from the prior Japanese Patent Application No. 2010-242162, filed Oct. 28, 2010, the entire contents of which is incorporated herein by reference.

BACKGROUND OF THE INVENTION

1. Field of the Invention

The present invention relates to a method and device for detecting an amount of particulate matter contained in a gas to be measured, such as an exhaust gas from vehicles, and in particular, the method and apparatus detect an amount of the particulate matter based on electrical resistance caused by the particulate matter accumulating between electrodes. The present invention also relates to a method of manufacturing a particulate matter detection element used in the particulate matter detecting device.

2. Description of the Related Art

The exhaust gas of a diesel engine of an automobile and the like may include environmental pollutants, particularly particulate matter (hereinafter referred to accordingly as "PM") mainly composed of soot particles and soluble organic fractions (SOF). A diesel particulate filter (hereinafter referred to accordingly as "DPF") is provided on an exhaust gas path to collect the PM. The DPF is made of a porous ceramic having excellent heat resistance. The DPF captures the PM as a result of the exhaust gas passing through a partition wall having numerous fine pores.

When the amount of collected PM exceeds an allowable amount, the DPF becomes clogged. Pressure loss may increase. Alternatively, the amount of PM escaping through the DPF may increase. Therefore, collection capability is recovered by a regeneration process being periodically performed.

In general, increase in the differential pressure across the DPF caused by increase in the amount of collected PM is used for determining the regeneration timing. Therefore, a differential pressure sensor is provided that detects the difference in pressure upstream and downstream from the DPF.

The regeneration process is performed by high-temperature exhaust gas being introduced into the DPF through heating using a heater, by post-injection, or the like, and the PM being removed by burning.

On the other hand, a sensor capable of directly detecting the PM in the exhaust gas has been proposed. The PM sensor is, for example, provided downstream from the DPF and measures the amount of PM escaping through the DPF. The PM sensor can be used in an on-board diagnosis (OBD) device to monitor an operating state of the DPF or to detect abnormalities such as cracks and damage.

Use of the PM sensor in place of the differential pressure sensor to determine the regeneration timing of the DPF is also being discussed. In this instance, the PM sensor is provided upstream from the DPF and measures the amount of PM entering the DPF.

As a basic configuration of a PM sensor such as that described above, JP-A-S59-197847 discloses an electrical-resistance-type smoke sensor. The smoke sensor is configured such that a pair of conductive electrodes are formed on a front surface of a substrate having insulating properties, and a heating element is formed on a back surface of or within the substrate. The smoke sensor takes advantage of smoke (particulate carbon) having conductivity, and detects changes in electrical resistance value occurring as a result of smoke accumulating between the electrodes that serve as a detection section.

In a particulate matter detecting device such as that described above, when a certain amount of particulate matter or more is accumulated between detection electrodes, the detected resistance no longer changes. The amount of particulate matter within gas to be measured can no longer be detected.

Therefore, the heating element that generates heat as a result of being energized is provided. The detection section is heated by being directly heated by a heater. Alternatively, the detection section is heated by post-injection or the like, by exhaust gas, serving as the gas to be measured, being heated to a high temperature. As a result, the particulate matter accumulated between the detection electrodes is removed by burning. Detection capability is thereby recovered.

In addition, WO 2008/031654 discloses an example of a particulate matter detection element, such as that described above, and a control method. The particulate matter detection element in WO 2008/031654 is configured such that a resistance layer is connected in parallel to electrical resistance formed by particulate matter accumulated between detection electrodes. The resistance layer is provided between a substrate and a pair of detection electrodes. The resistance layer is formed by a conductive layer containing zirconia or the like. As a result of the resistance layer being formed, damage and deterioration of the electrodes can be detected.

However, in a conventional electrical-resistance-type particulate matter detecting device, such as that described in JP-A-S59-197847, when the particulate matter accumulated between detection electrodes is heated and removed, the resistance between the detection electrodes becomes extremely high, causing an almost insulated state.

Therefore, it may be difficult to use the value of the detected resistance to differentiate between a state in which particulate matter is not accumulated between the detection electrodes, and a state in which a disconnection abnormality has occurred in an electrical wire of a signal line connecting a detection element and a detection circuit or the like.

As described in WO 2008/031654, energization is performed between the detection electrodes by the conductive layer. Therefore, output is detected even in a state in which particulate matter is not accumulated, if the resistance value of the conductive layer is too low. As a result, malfunction may occur. Furthermore, the resistance value of the conductive layer is required to be adjusted with high accuracy, leading to increase in manufacturing cost.

Moreover, the metal configuring the detection electrodes inevitably becomes dispersed in the conductive layer as a result of extended use. The resistance value of the conductive layer changes, thereby causing instable output.

SUMMARY

The present invention has been achieved in light of the above-described issues. An object of the present invention is to provide an electrical-resistance-type particulate matter detecting device used to detect particulate matter within exhaust gas of an internal combustion engine. The particulate matter detecting device is highly reliable, having high detection accuracy and being capable of detecting disconnection abnormality. The present invention also provides a method of manufacturing a particulate matter detection element used in the particulate matter detecting device. The present invention also provides a method of detecting disconnection in a particulate matter detecting device.

According to a first aspect, A detecting device is provided that detects an amount of particulate matter included in a gas to be measured, the detecting device having:

a detection element having a detection section that has electrical resistance in relation to the particulate matter against a direct current and a capacitance component;

a detection circuit having an alternating-current power source that supplies an alternating current to the detection element and an alternating-current detector that detects the alternating current flowing through the detection element.

According to the first aspect, the capacitance component becomes a predetermined value proportional to a relative permittivity of the dielectric layer and the area of parallel plate conductors and inversely proportional to the film thickness of the dielectric layer. The capacitance component indicates impedance of a certain range in relation to the alternating current supplied from the alternating current power source.

Even in a state in which the particulate matter is not accumulated between the detection electrodes, the direct current applied by the direct current power source is not flowing through the particulate matter detection element, and output from a direct-current detector cannot be detected, the alternating-current detector can detect the alternating current transmitted via the capacitance component.

Therefore, when disconnection abnormality occurs between the detection circuit and the particulate matter detection element connected via a signal line, the alternating current detected by the alternating-current detector changes. The disconnection abnormality can be promptly detected.

As a result of the direct-current detector detecting the direct current flowing to the particulate matter detection element, detection resistance formed by the particulate matter accumulated between the detection electrodes can be accurately measured.

At this time, as a result of an insulating ceramic being used as the dielectric layer, the direct current resistance between the parallel plate conductors can be increased and insulation properties can be ensured in the capacitance component. Therefore, the amount of particulate matter accumulated in the detection section can be stably detected without the direct current flowing to the capacitance component and without the output of the detected resistance detected by the direct-current detector being affected.

BRIEF DESCRIPTION OF THE DRAWINGS

In the accompanying drawings:

FIG. 13 is a flowchart of an example of disconnection detection and particulate matter detection according to the first embodiment.

DETAILED DESCRIPTION OF THE PREFERRED EMBODIMENTS

Figure 1:
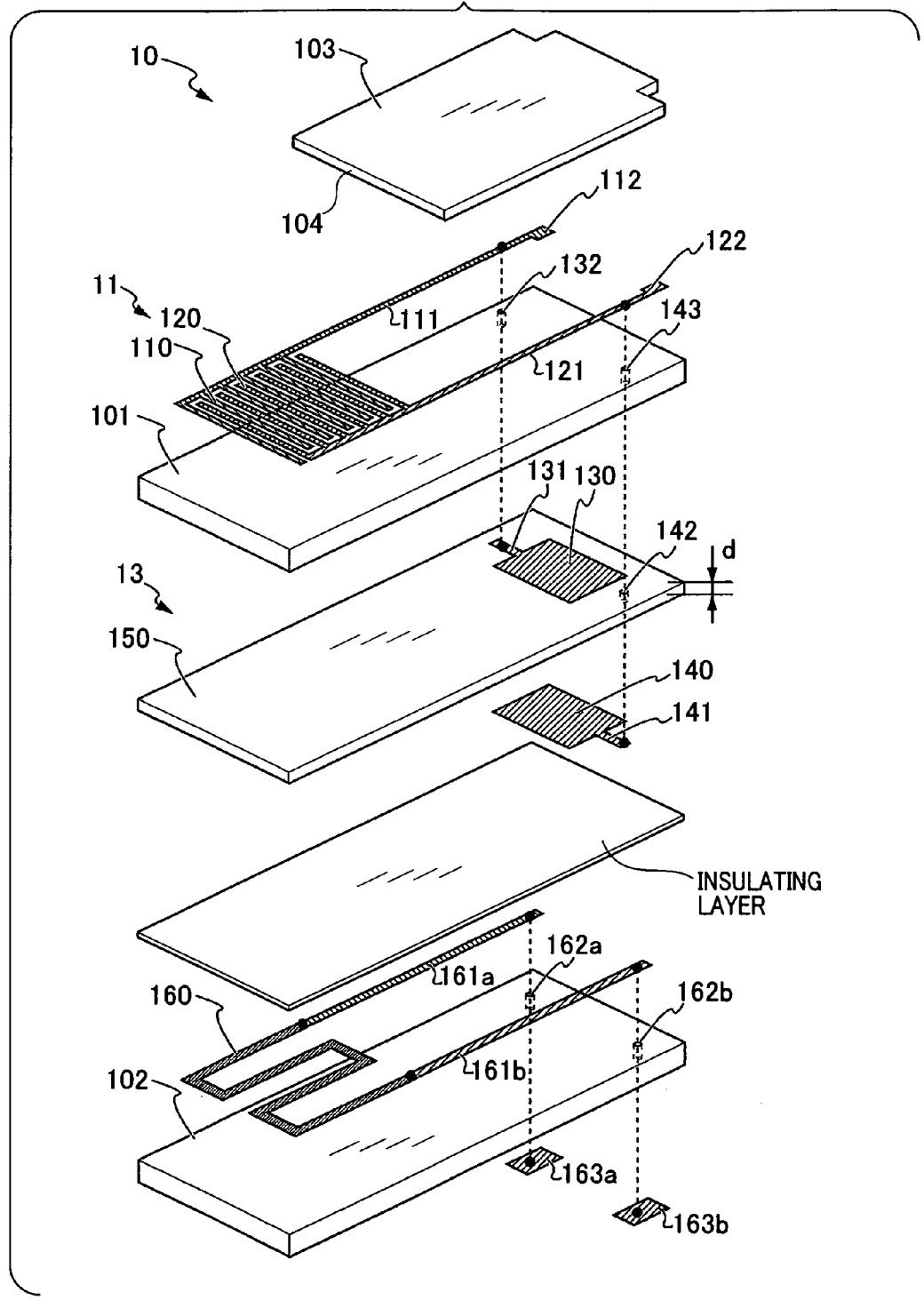
FIG. 1 is an exploded perspective view of an overview of a particulate matter detection element used in a particulate matter detecting device according to a first embodiment of the present invention.

A particulate matter detecting device according to various preferred embodiments of the present invention will hereinafter be described with reference to the accompanying drawings.

First Embodiment

A first embodiment will be described with reference to FIG. 1 to FIGS. 9A and 9B, and FIG. 13.

A particulate matter detecting device 100 according to the first embodiment of the present embodiment is provided on an exhaust gas flow path of an internal combustion engine. The exhaust gas serves as the gas to be measured. The particulate matter detecting device 100 detects the amount of particulate matter within the gas to be measured. Combustion control of the internal combustion engine, regeneration of an exhaust emission control device, abnormality diagnosis, and the like are performed using the detection result.

The particulate matter detecting device 100 includes at least a particulate matter detection element 10 and a detection circuit 20. The particulate matter detection element 10 is provided with a pair of detection electrodes 110 and 120 serving as a detection section 11. The pair of detection electrodes 110 and 120 are provided such as to oppose each other with a predetermined amount of space therebetween on a front surface of an insulating substrate 101. The detection circuit 20 is connected to the particulate matter detection element 10 by a pair of signal lines 116 and 126 (see FIG. 4A). The detection circuit 20 detects electrical resistance formed by particulate matter PM accumulated in the detection section 11 as detected resistance $R_{SEN}$. In the particulate matter detecting device 100 that detects the amount of particulate matter PM included within the gas to be measured, the particulate matter detection element 10 includes a capacitance component 13 disposed in parallel with the detected resistance $R_{SEN}$. Furthermore, the detection circuit 20 includes a direct-current power source 21, an alternating-current power source 22, a direct-current detector 23, and an alternating-current detector 24. The direct-current power source 21 supplies a direct current $I_{DC}$ to the particulate matter detection element 10. The alternating-current power source 22 supplies an alternating current $I_{AC}$ having a predetermined frequency f and a predetermined amplitude. The direct-current detector 23 detects the direct current $I_{DC}$ flowing to the particulate matter detection element 10. The alternating-current detector 24 detects the alternating current $I_{AC}$. The capacitance component 13 is formed by an insulating ceramic serving as a dielectric layer 150 and a pair of parallel plate conductors 130 and 140. The dielectric layer 150 has a predetermined film thickness d and a predetermined relative permittivity $\in_r$. The pair of parallel plate conductors 130 and 140 have a predetermined area S and are disposed such as to oppose each other with the dielectric layer 150 therebetween.

In a state in which the particulate matter is not accumulated between the detection electrodes 110 and 120, the capacitance component 13 is connected in series between the detection electrodes 110 and 120. As a result, disconnection D1 in the detection section 11 can be detected in addition to disconnection D2 between the detection section 11 and the detection circuit 20.

An overview of the particulate matter detection element 10 will be described with reference to FIG. 1.

The particulate matter detection element 10 has the insulating substrate 101 and the detection section 11. The particulate matter detection element 10 has the pair of detection electrodes 110 and 120, a pair of detection lead sections 111 and 121, and detection terminal sections 112 and 122. The pair of detection electrodes 110 and 120 are formed on the front surface of the insulating substrate 101. The pair of detection lead sections 111 and 121 are formed connected to the detection electrodes 110 and 120. The detection terminal sections 112 and 122 are formed respectively connected to the detection lead sections 111 and 121.

The insulating substrate 101 is formed into a rough plate shape by a known method, such as a doctor blade method, using an insulating heat-resistant material such as alumina.

The detection electrodes 110 and 120, the detection lead sections 111 and 121, and the detection terminal sections 112 and 122 are formed by a known method, such as thick film printing, using a conductive material such as platinum.

Furthermore, the capacitance component 13 that is a main section of the present embodiment is formed such as to be layered on the rear-surface side of the insulating substrate 101.

The capacitance component 13 has the dielectric layer 150 and the pair of plate conductors 130 and 140. The dielectric layer 150 is formed in a rough plate shape, having a predetermined film thickness d. The dielectric layer 150 is formed using an insulating ceramic having a predetermined relative permittivity $\in_r$, such as alumina. The pair of plate conductors 130 and 140 are formed such as to oppose each other and have a predetermined area S. The pair of plate conductors 130 and 140 are formed on either side of the dielectric layer 150 such as to sandwich the dielectric layer 150. The plate conductors 130 and 140 are respectively connected to conductor lead sections 131 and 141. The plate conductors 130 and 140 are also connected to the detection lead sections 111 and 121 via the conductor lead sections 131 and 141, through-hole electrodes 132, 142, and 143 that pass through the dielectric layer 150 and the insulating substrate 101. As a result, the capacitance component 13 is parallel with the detected resistance $R_{SEN}$.

The plate conductors 130 and 140 configure parallel plate conductors that oppose each other with the dielectric layer 150 having a thickness d therebetween, thereby forming the capacitance component 13.

Capacitance $C_{13}$ of the capacitance component 13 is $C_{13}=\in_r\in_0 S/d$, when relative permittivity is $\in_r$, vacuum permittivity is $\in_0$, the area of the plate conductors 130 and 140 is S, and the thickness of the dielectric layer 150 is d.

An alternating current impedance Z of the capacitance component 13 is expressed by $Z=1/j\omega C_{13}$ (j being an imaginary unit). An absolute value |Z| of the alternating current impedance Z is expressed by $1/\omega C_{13}=1/(2\pi \cdot f \cdot C_{13})$ (f being a frequency of the alternating current that is applied).

According to the first embodiment, the area S of the plate conductors 130 and 140 and the film thickness d of the dielectric layer 150 are formed such that the absolute value of the alternating current impedance Z is 200 kΩ or less.

In other words, when the area S of the plate conductors 130 and 140 is 10 (mm$_2$), the relative permittivity $\in_r$ of alumina configuring the dielectric layer 150 is 11.2, and the frequency f of the alternating current applied by the alternating-current power supply 22, described hereafter, is 20 kHz, $C_{13}$ is $1000/8/\pi=39.8$ pF or more. In other words, the film thickness d is formed to be $11.2\times 8.854\times 10/39.8=24.9$ μm or less.

In addition, according to the first embodiment, the dielectric layer 150 is formed having a film thickness d such that direct current resistance $R_{150}$ of the dielectric layer 150 is 1 MΩ or more, using an insulating ceramic having a volume resistivity p that is $1.4\times 10^{11}$ (Ωm) or more at a temperature of 600° C.

In other words, according to the first embodiment, a relationship is established in which $d \geq 7$ (μm).

Here, a procedure for forming the capacitance component 13 that is a main section of the method of manufacturing the particulate matter detection element 10 of the present embodiment will be described.

The dielectric layer 150 is formed by an insulating ceramic mixing and dispersing procedure and a dielectric layer forming procedure being performed. In the insulating ceramic mixing and dispersing procedure, insulating ceramic powder having a predetermined relative permittivity $\in_r$ and a predetermined volume resistivity p, a predetermined dispersion medium, a predetermined binder, and a predetermined plasticizer are mixed and dispersed into a slurry state or a paste state. In the dielectric layer forming procedure, the ceramic slurry or the ceramic paste obtained by the insulating ceramic mixing and dispersing procedure is used to form the dielectric layer 150 by coating or printing.

According to the first embodiment, the roughly plate-shaped dielectric layer 150 having a predetermined film thickness d is formed by the doctor blade method, using a slurry formed by the insulating ceramic being dispersed in a predetermined dispersing medium or the like.

In a first plate conductor forming procedure, on one surface of the dielectric layer 150 formed in a rough plate shape, the first plate conductor 130 having a predetermined area S and the first conductor lead section 131 are formed by printing, using a metal paste composed of Pt or the like. Furthermore, in a second plate conductor forming procedure, on the other surface of the dielectric layer 150, the second plate conductor 140 having a predetermined area S and the second conductor lead section 141 are formed by printing, using a metal paste composed of Pt or the like.

The through-hole electrode 132 is formed by a through-hole being filled with an electrode paste composed of Pt or the like. The through-hole is provided such as to pass through the rear-surface side and the front-surface side of the insulating substrate 101 to connect the first conductor lead section 131 and the detection lead section 111.

In addition, the through-hole electrode 143 is formed by a through-hole being filled with the electrode paste. The through-hole is provided such as to pass through the rear-surface side and the front-surface side of the insulating substrate 101 to connect the second conductor lead section 141 and the detection lead section 121. Furthermore, the through-hole electrode 142 is formed by a through-hole being filled with an electrode paste composed of Pt or the like. The through-hole is provided such as to pass through the rear-surface side and the front-surface side of the dielectric layer 150.

As a result of the foregoing components being integrally layered, the pair of parallel plate conductors are formed such that the plate conductor 130 and the plate conductor 140 oppose each other with the dielectric layer 150 therebetween. The plate conductors 130 and 140 are respectively connected to the detection lead sections 111 and 121. The capacitance component 13 is connected in parallel to the detected resistance RSEN.

Furthermore, an insulating substrate 102 is disposed such as to be layered on the rear-surface side of the dielectric layer 150. A heating element 160 and a pair of heating element lead sections 161a and 161b connected to the heating element 160 are formed on the insulating substrate 102. An insulating substrate to ensure insulation between the second plate conductor 140 and the heating element lead sections 161a and 161b is formed in a rough plate shape in a manner similar to the insulating substrate 101 on the insulating substrate 101, for example by printing alumina paste, so that the heating element 160 and the heating element lead sections 161a and 161b are covered. Furthermore, a pair of through-hole electrodes 162a and 162b are formed such as to pass through the insulating substrate 102. The pair of through-hole electrodes 162a and 162b are connected to the heating element lead sections 161a and 161b. A pair of heating element terminal sections 163a and 163b are formed on the rear-surface side of the insulating substrate 102 such as to be connected to the through-hole electrodes 162a and 162b.

Furthermore, a protective layer 103 is formed such as to be layered on the detection electrodes 110 and 120 and to cover the detection lead sections 111 and 121. The protective layer 103 is formed using heat-resistant glass and insulating ceramic. An opening section 104 from which the detection section 11 is exposed is provided in the protective layer 103.

The protective layer 103 protects the detection lead sections 111 and 121, and prevents malfunction caused by accumulation of the particulate matter PM in areas other than the detection section 11.

The integrated particulate matter detection element 10 is completed by the compact having a laminated structure obtained by the above-described manufacturing procedures being fired. When manufacturing is performed as described above, the capacitance component 13 can be integrally formed with significant ease when forming the particulate matter detection element 10. For example, unlike in the above-described manufacturing method, the capacitance component may be mounted once the particulate material detection element is formed. However, when the above-described manufacturing method is used, the number of manufacturing procedures and manufacturing cost can be reduced.

In addition, the relative permittivity of the insulating ceramic to be used, the film thickness of the dielectric layer 150 to be formed, and the area of the parallel plate conductors 130 and 140 can be arbitrarily set. Therefore, the alternating current impedance of the particulate matter detection element 10 can be easily controlled to a desired value.

Figure 2:
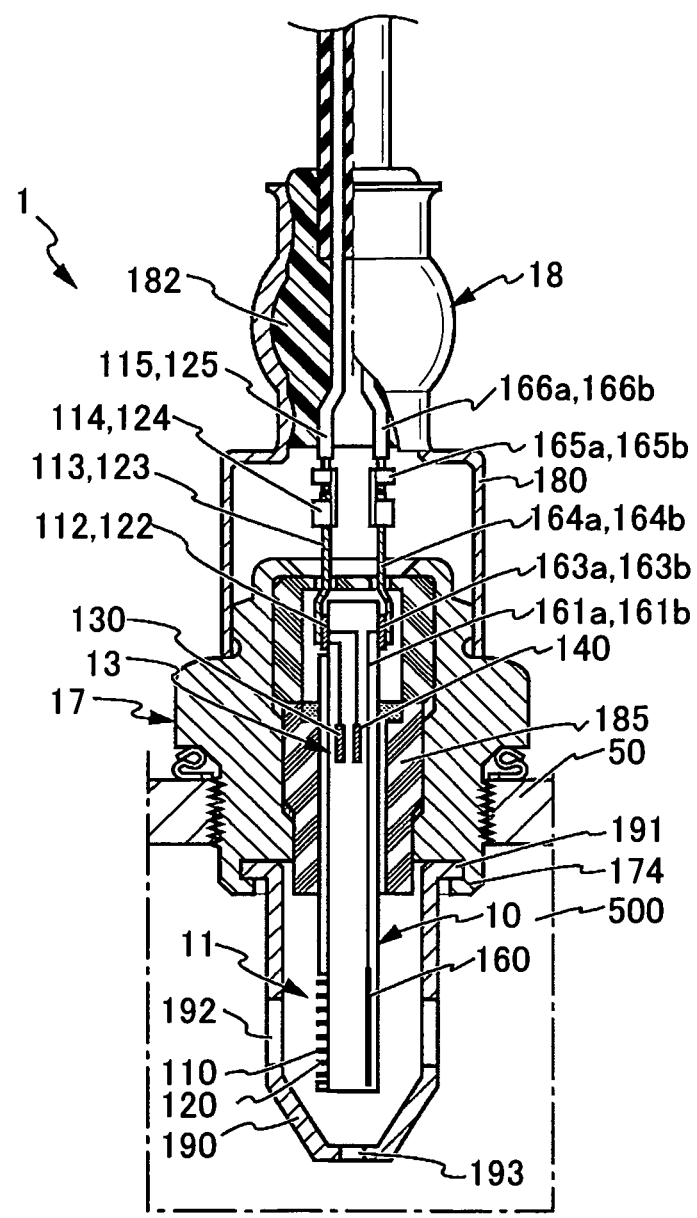
FIG. 2 is a cross-sectional view of an example of a particulate matter detection sensor used in the particulate matter detecting device according to the first embodiment of the present invention.

A particulate matter detection sensor 1 provided in the particulate matter detection element 10 of the present embodiment will be described with reference to FIG. 2.

The particulate matter detection sensor 1 includes a roughly cylindrical insulator 185 and a housing 17. The particulate matter detection element 10 is inserted and held within the insulator 185. The housing 17 is fixed to a flow path wall 50 of the flow path through which the gas to be measured flows. The housing 17 holds the insulator 185 and holds the detection section 11 of the particulate matter detection element 10 in a predetermined position within a measuring flow path 500. Furthermore, the particulate matter detection sensor 1 includes a cover body 190 and a roughly cylindrical casing 19. The cover body 190 is provided on the tip-end side of the housing 17 and protects the detection section 11 of the particulate matter detection element 10. The casing 18 is provided on the base-end side of the housing 17. A pair of signal lines 115 and 125 are inserted into the casing 18 via a sealing member 182. The signal lines 115 and 125 are connected to the detection terminal sections 112 and 122 of the particulate matter detection element 10 by connection fittings 113, 114, 123, and 124. The signal lines 115 and 125 transmit the detected electrical resistance $R_{SEN}$ between the detection electrodes 110 and 120 to the external detection circuit 20. The detected electrical resistance $R_{SEN}$ changes depending on the amount of PM collected and accumulated in the detection section 11. In addition, a pair of conduction lines 166a and 166b are inserted into the casing 18. The conduction lines 166a and 166b are connected at one end to the heating element 160 within the particulate matter detection element 10, via the heating element terminal sections 163a and 163b and connection fittings 164a, 164b, 165a, and 165b. The conduction lines 166a and 166b are connected at the other end to a heating element control device 30.

Measured gas inlet/outlet holes 192 and 193 are formed accordingly in the cover body 190. The gas to be measured that includes the PM is introduced into the detection section 11 through the measured gas inlet/outlet holes 192 and 193. A flange section 191 provided on a base-end side of the cover body 190 is clumped and fixed by a clumping section 174 provided at the tip-end side of the housing 17.

According to the first embodiment, the capacitance component 13 is included in the particulate matter detection element 10 and disposed in a position within the insulator 185 where the temperature is stable at 500° C. or below. As a result of the capacitance component 13 being disposed in the position where the temperature is 500° C. or below, insulation resistance of the insulating ceramic configuring the dielectric layer 150 does not decrease to 1 MΩ or less by receiving heat from ambient temperature. The configuration is therefore preferable.

The gas to be measured that includes the particulate matter PM flows through the measured gas flow path 500, and is introduced from the measured gas inlet/outlet holes 192 provided in the cover body 190. The gas to be measured comes into contact with the front surface of the detection section 11 of the particulate matter detection element 10 that exposes the detection section 11 to the gas to be measured. As a result, the PM accumulates between the detection electrodes 110 and 120.

An overview of the overall particulate matter detecting device 100 using the particulate matter detection element 10 of the present embodiment will be described with reference to FIG. 3.

With the electrical resistance formed by the particulate matter accumulated between the detection electrodes 120 and 130 configuring the detection section 11 of the particulate matter detection element 10 serving as the detected resistance $R_{SEN}$, the capacitance component 13 is connected in parallel to the detected resistance $R_{SEN}$.

The detection circuit 20 is provided with the direct-current power source 21, the alternating-current power source 22, the direct-current detector 23, and the alternating-current detector 24. The direct-current power source 21 applies the direct current $I_{DC}$ to the particulate matter detection element 10. The alternating-current power source 22 applies the alternating current $I_{AC}$. The direct-current detector 23 detects the direct current $I_{DC}$ flowing to the detected resistance $R_{SEN}$. The alternating-current detector 24 detects the alternating current $I_{AC}$ flowing via the capacitance component 13.

When the particulate matter PM accumulates between the detection electrodes 110 and 120, and the detected resistance $R_{SEN}$ is formed, the direct current $I_{DC}$ based on the detected resistance $R_{SEN}$ flows in relation to a direct current voltage $V_{DC}$ applied by the direct-current power source 21. The direct-current detector 23 detects the direct current $I_{DC}$. The amount of particulate matter PM accumulated in the detection section 11 can be calculated from the change in direct current $I_{DC}$.

Furthermore, the alternating current $I_{AC}$ flows via the capacitance component 13 in relation to an alternating current voltage $V_{AC}$ applied by the alternating-current power source 22. The alternating-current detector 24 detects the alternating current $I_{AC}$. As a result, a disconnection abnormality can be detected that occurs between the particulate matter detection element 10 and the detection circuit 20 connected by the detection lead sections 111 and 121, the detection terminal sections 112 and 122, the connection fittings 113, 114, 123, and 124, and the signal lines 115 and 125.

The heating element 160 is connected at one end to a drive power source 31 from the heating element lead section 161a via the conduction line 166a. The heating element 160 is grounded at the other end via the heating element lead section 161b, the conduction line 166b, an open/close element 320, and a current detecting means 330. The open/close element 320 is provided in the heating element control device 30 and is controlled such as to open and close by a driving section 32. The current detecting means 330 detects the current flowing to the heating element 160. A temperature detection section 33 detects the temperature of the heating element 160 based on resistance of the heating element 160 detected by the current detecting means 330. Temperature control of the heating element 160 is performed using the detected temperature.

A semiconductor, such as a metal-oxide-semiconductor field-effect transistor (MOSFET), is used as the open/close element 320. The open/close element 320 is opened and closed in adherence to drive signals sent from the driving section 32. The open/close element 320 supplies a pulsed current to the heating element 160, and adjusts the amount of generated heat by controlling the duty ratio of energization pulses. The amount of generated heat to be adjusted is set based on the temperature of the heating element 160 detected by the temperature detection section 33 and the like.

A first test conducted to confirm the effects of the present embodiment will be described with reference to FIG. 4A to FIG. 4D.

Figure 4A:
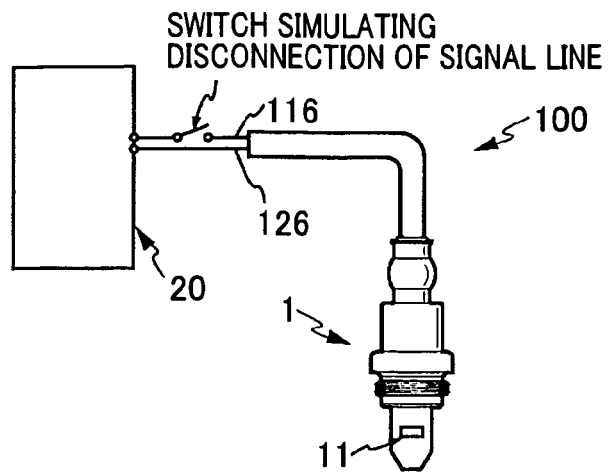
FIG. 4A is an explanatory diagram of an overview of a method of a first test conducted to confirm the effects of the present invention.

As shown in FIG. 4A, an open/close switch SW is provided between the signal lines 116 and 126 connecting the particulate matter detection sensor 1 including the particulate matter detection element 10 of the present embodiment and the detection circuit 20. The open/close switch SW simulates a disconnection. The changes in the direct current $I_{DC}$ and the alternating current $I_{AC}$ detected when the switch SW is opened and closed were examined. The direct current $I_{DC}$ and the alternating current $I_{AC}$ flowing through the particulate matter detection element 10 are changed into voltage by the direct-current detector 23 and the alternating-current detector 24, and the direct-current detector 23 and output voltage from the alternating-current detector 24 are obtained as result of the first test.

Figure 4B:
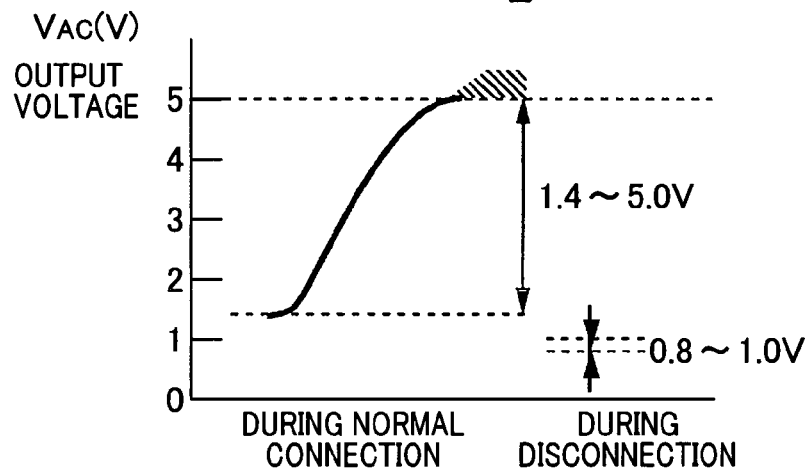
FIG. 4B is a characteristics diagram showing changes in output voltage detected by an alternating-current detector.

As shown in FIG. 4B, in a normal state, complex impedance of the detected resistance $R_{SEN}$ and the capacitance C13 of the capacitance component 13 changes based on the changes in the amount of PM accumulated in the detection section 11 of the particulate matter detection element 10 and the temperature of the particulate matter detection element 10. The output voltage $V_{AC}$ detected by the alternating-current detector 24 changes between about 1.4V to 5V. On the other hand, during disconnection, the output voltage $V_{AC}$ is about 0.8V to 1.0V.

Figure 4C:
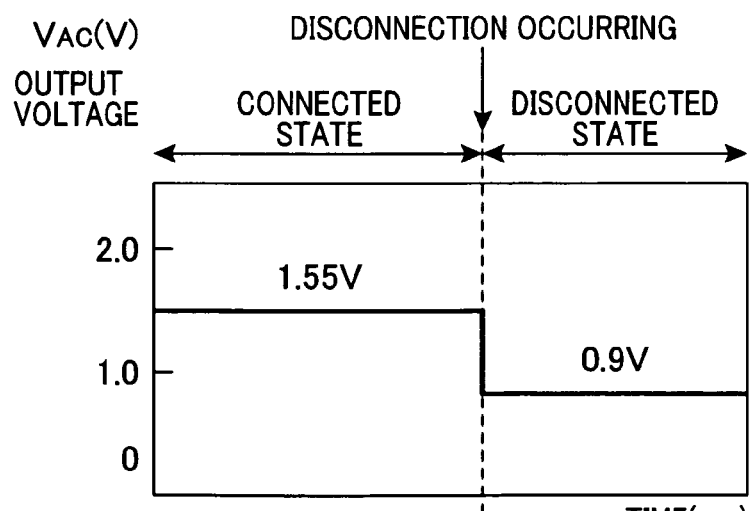
FIG. 4C is a characteristics diagram showing differences in output voltage in a connected state and a disconnected state detected in the first test.
Figure 4D:
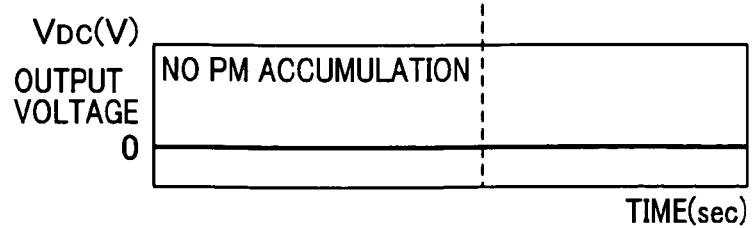
FIG. 4D is a characteristics diagram showing output voltage of a direct-current detector detected in the first test.

Then, the heating element 160 was energized. In a state in which the PM is not accumulated in the detection section 11, the open/close switch SW simulating disconnection was changed from a closed state to an open state. As a result, as shown in FIG. 4C, the output from the alternating-current detector 24 indicates 1.55V in the state in which the switch SW is closed and a normal connection is simulated. In a state in which the switch is opened and disconnection is simulated, the output changes to 0.9V. Normal connection and disconnection are clearly differentiated. On the other hand, as shown in FIG. 4D, the output from the direct-current detector 23 in a state in which the PM is not accumulated in the detection section 11 was not detected, regardless of the opening and closing of the switch SW, because conduction does not occur between the detection electrodes 110 and 120.

Confirmation has been made that, when the particulate matter detection element 10 of the present embodiment is used in this way, disconnection abnormality occurring in the signal lines 116 and 126 can be clearly detected by detection of the alternating current $I_{AC}$, regardless of the accumulation state, including the state in which the PM is not accumulated in the detection section 11.

FIG. 13 is an example of an operational flow for disconnection detection and particulate matter detection using the particulate matter detection element 10. First, an alternating current is applied to the particulate matte detection element 10 by the alternating-current power source 22 (Step S101).

The alternating-current detector 24 detects the alternating current (such as the alternating current voltage value) (Step S102). Then, based on the detected value, a calculating section 6 performs comparison with a threshold value for judging whether disconnection has occurred that has been determined in advance, and judgment regarding whether disconnection has occurred is made (Step S103). For example, disconnection is judged to have occurred when an effective value of the voltage is lower than the predetermined threshold value.

Next, a direct current is applied to the particulate matter detection element 10 by the direct-current power source at a predetermined timing (such as when judged that disconnection has not occurred at Step S103) (Step S104). The direct-current detector 23 detects the direct current (Step S105). Based on the detected direct current, the calculating section 26 calculates the amount of particulate matter (Step S106).

The application of the present embodiment is not limited to the above-described operational flow. For example, the direct current and the alternating current may be superimposed. Judgment regarding disconnection and particulate matter detection may be simultaneously performed.

Figure 3:
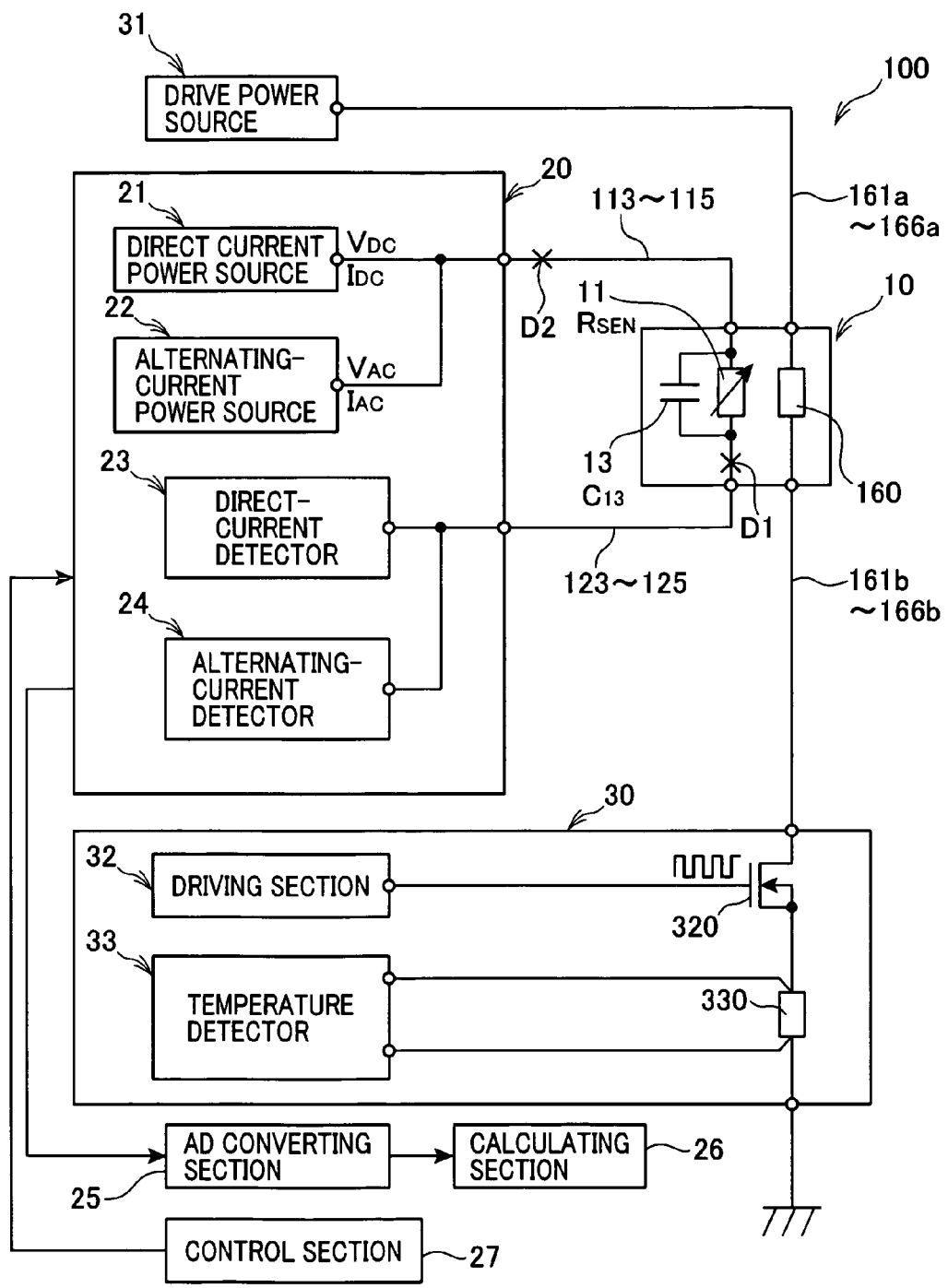
FIG. 3 is a block diagram of an overview of the overall particulate matter detection sensor according to the first embodiment of the present invention.

A control section 27 in FIG. 3 outputs operation commands at predetermined timings to the direct-current power source 21, the alternating-current power source 22, the direct-current detector 23, and the alternating-current detector 24. The control section 27 is configured by an oscillator or the like. An analog-to-digital (AD) converting section 25 converts the detected values from the direct-current detector 23 and the alternating-current detector 24 to digital signals, and outputs the digital signals to the calculating section 26.

A test conducted on the insulating ceramic used in the dielectric layer 150 of the particulate matter detection element 10 according to the first embodiment will be described with reference to FIG. 5A to FIG. 9B.

Figure 5A:
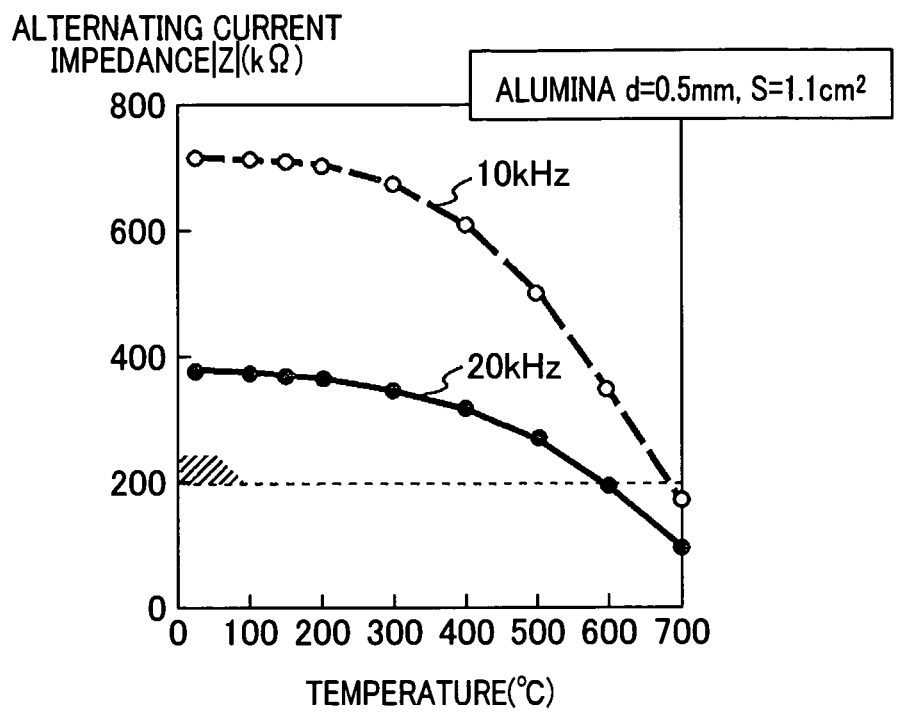
FIG. 5A is a characteristics diagram showing changes in alternating current impedance depending on temperature changes when alumina is used in a dielectric layer.
Figure 5B:
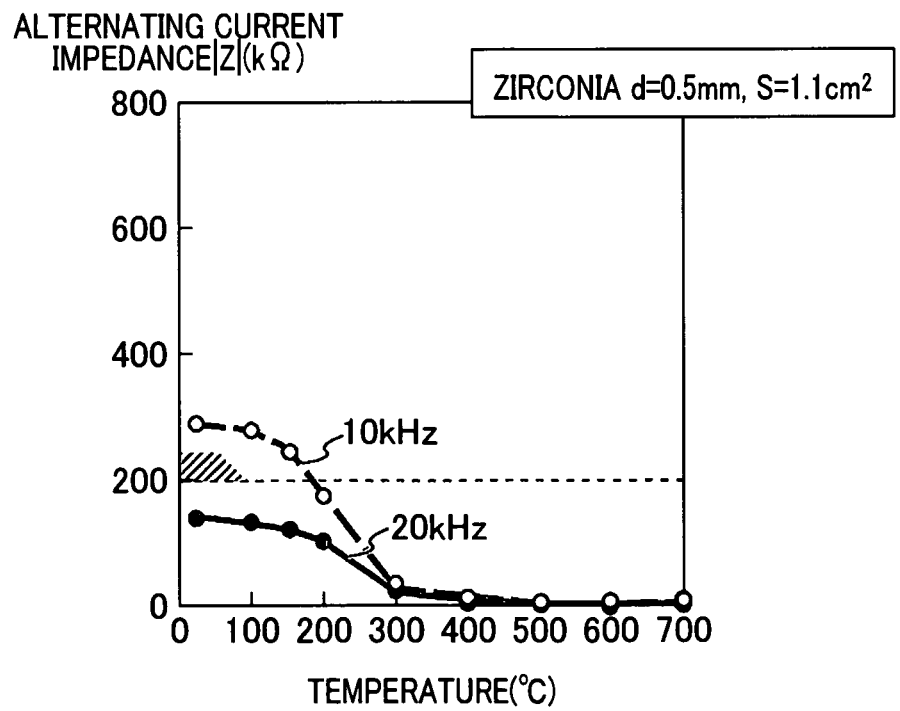
FIG. 5B is a characteristics diagram of changes in alternating current impedance depending on temperature changes when zirconia is used in the dielectric layer.

FIG. 5A shows the results of a preliminary test conducted in an instance in which the dielectric layer 150 is composed of alumina. In the preliminary test, a plate conductor of which the area S is 1.1 cm$^2$ was formed on both surfaces of an alumina substrate of which the relative permittivity $\in_r$ is 11.2 and the thickness d is 0.5 mm. Sweeping was performed using alternating currents of 10 kHz and 20 kHz. The changes in alternating current impedance |Z| when measurement temperature is changed from room temperature to 700° C. were examined using an impedance analyzer. FIG. 5B shows the results of a preliminary test conducted in an instance in which the dielectric layer 150 is composed of zirconia. In the preliminary test, a plate conductor of which the area S is 1.1 cm$^2$ was formed on both surfaces of an zirconia substrate of which the relative permittivity $\in_r$ is 12.5 and the thickness d is 0.5 mm. Sweeping was performed using alternating currents of 10 kHz and 20 kHz. The changes in alternating current impedance |Z| when measurement temperature is changed were examined.

As shown in FIG. 5A and FIG. 5B, in both instances, a decrease in alternating current impedance was observed in accompaniment with temperature increase.

When the actual particulate matter detection element 10 is used, the alternating current impedance enabling the alternating-current detector 24 to easily and accurately detect the alternating current or voltage is preferably 200 kΩ or less. However, when alumina is used, it is assumed that the alternating current impedance becomes too high and detection of the alternating current or voltage becomes difficult if the thickness d of the dielectric layer 150 is 0.5 mm.

On the other hand, when zirconia is used, if the alternating current used for sweeping is 20 kHz, the alternating current impedance is 200 kΩ or less in all temperature ranges even when the thickness d is 0.5 mm. However, when the temperature becomes higher than 300° C. at which the particulate matter detection element 10 is used, the alternating current impedance may become too low and detection of the alternating current or voltage may no longer be possible, regardless of frequency.

Figure 6A:
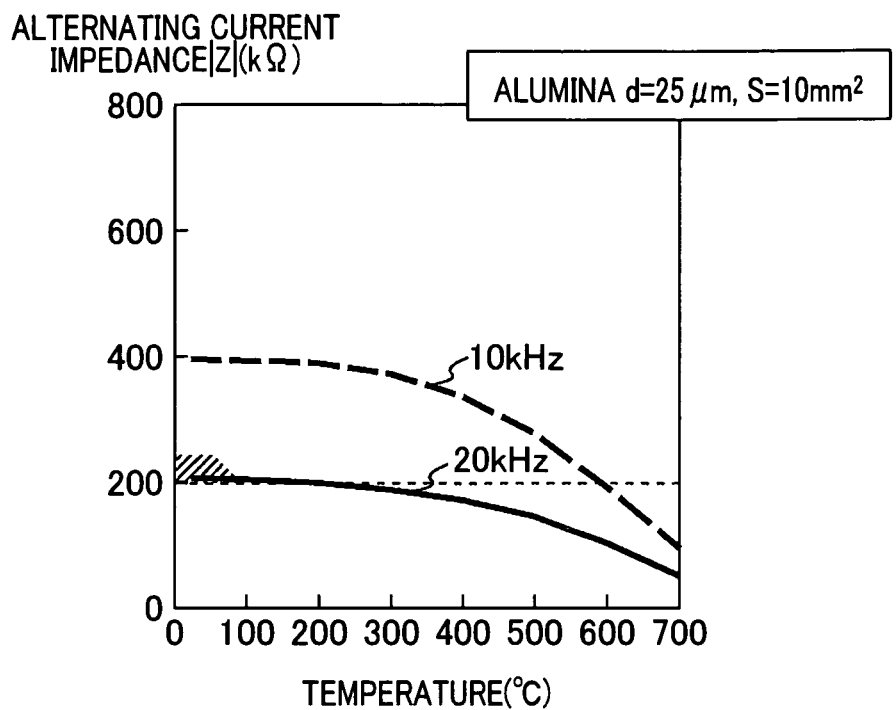
FIG. 6A is a characteristics diagram of changes in alternating current impedance depending on temperature changes when the thickness of the dielectric layer using alumina is 25 µm.
Figure 6B:
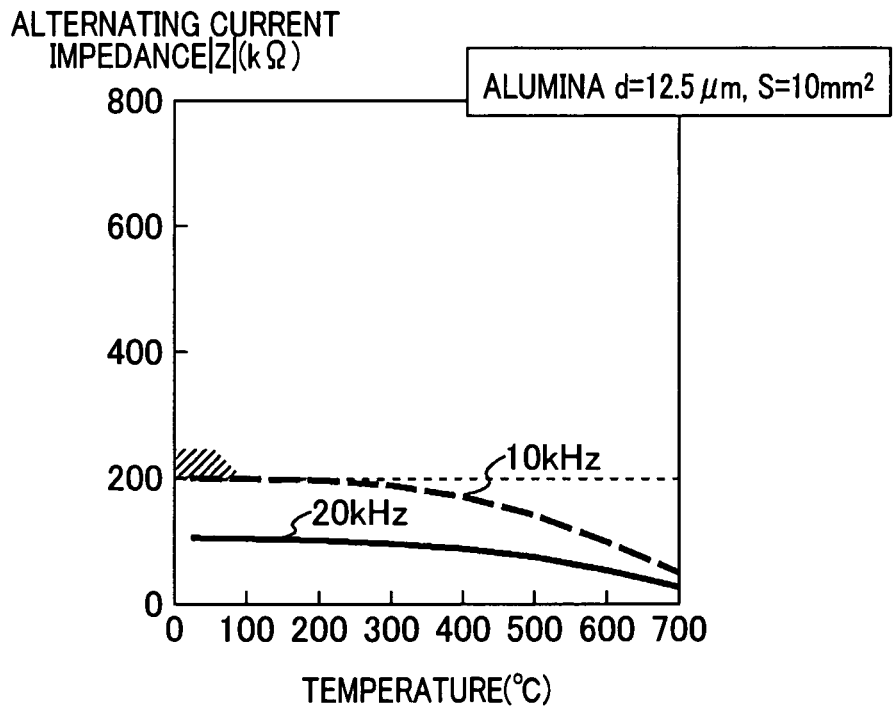
FIG. 6B is a characteristics diagram of changes in alternating current impedance depending on temperature changes when the thickness of the dielectric layer is 12.5 µm.

FIG. 6A and FIG. 6B show temperature changes in alternating current impedance in an instance in which the dielectric layer 150 is composed of alumina, and the thickness d of the dielectric layer 150 is 25 μm or 12.5 μm.

As shown in FIG. 6A, when the thickness d is set to 25 μm and the frequency used for sweeping is 20 kHz, the alternating current impedance becomes 200 kΩ or less in the temperature range of room temperature to 700° C. Detection is expected to be easily performed.

As shown in FIG. 6B, when the thickness d is set to 12.5 μm, regardless of the frequency used for sweeping, the alternating current impedance becomes 200 kΩ or less in the temperature range of room temperature to 700° C. Detection is expected to be easily performed.

Figure 7A:
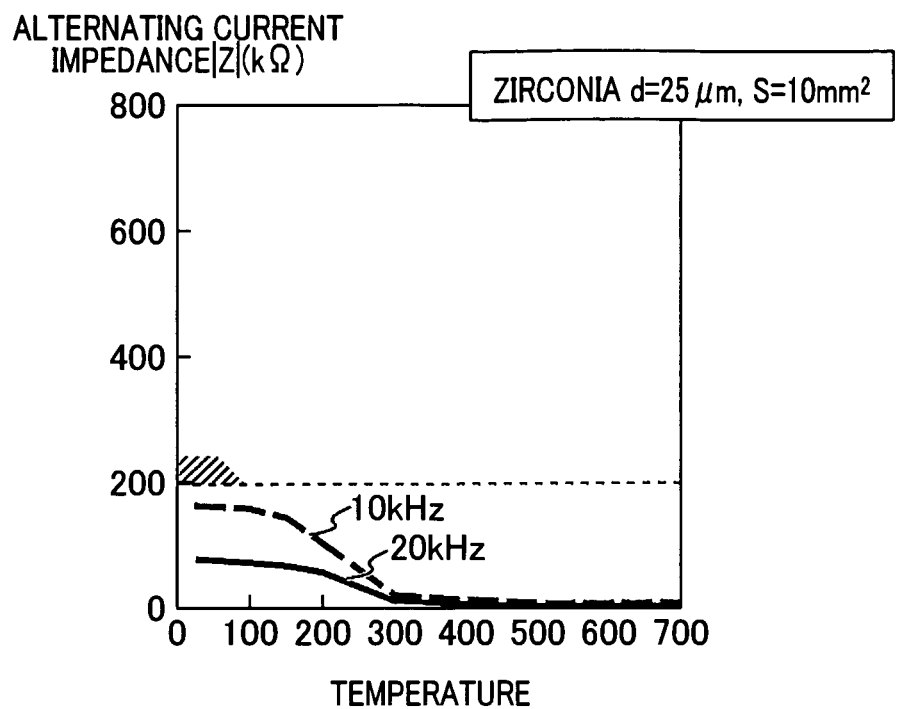
FIG. 7A is a characteristics diagram of changes in alternating current impedance depending on temperature changes when the thickness of the dielectric layer using zirconia is 25 µm.
Figure 7B:
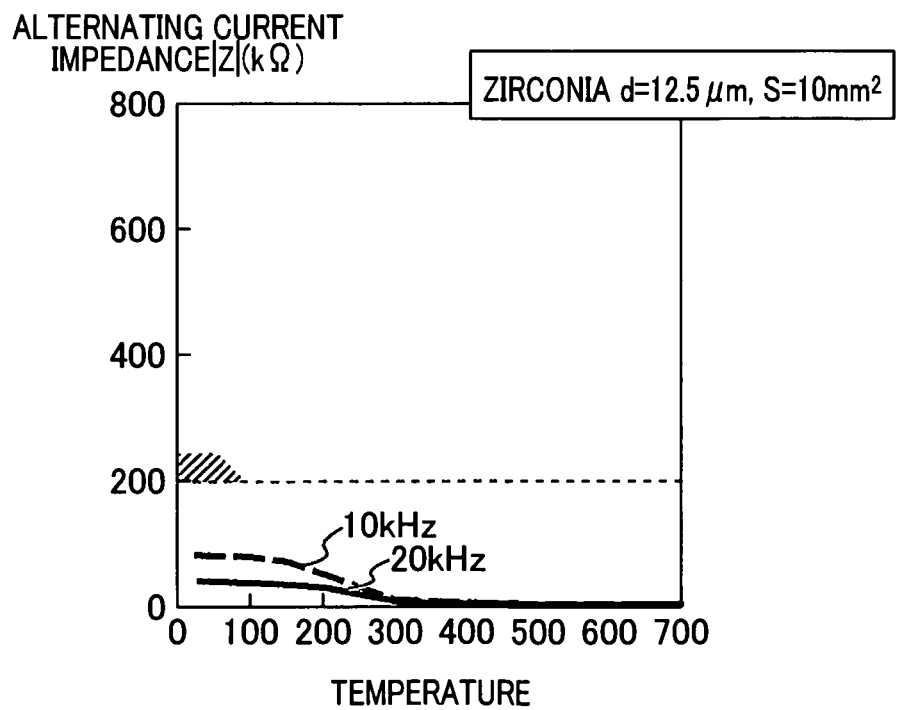
FIG. 7B is a characteristics diagram of changes in alternating current impedance depending on temperature changes when the thickness of the dielectric layer is 12.5 µm.

On the other hand, in an instance in which zirconia is used, when the thickness d of the dielectric layer 150 is 25 μm or 12.5 μm, as shown in FIG. 7A and FIG. 7B, detection is possible from room temperature to 300° C. in both instances. However, when the temperature becomes higher than 300° C. at which the particulate matter detection element 10 is used, the impedance becomes too low and detection of the alternating current or voltage is no longer possible.

Results of further examination of the effects in an instance in which alumina is used in the dielectric layer 150 will be described with reference to FIG. 8A and FIG. 8B.

Figure 8A:
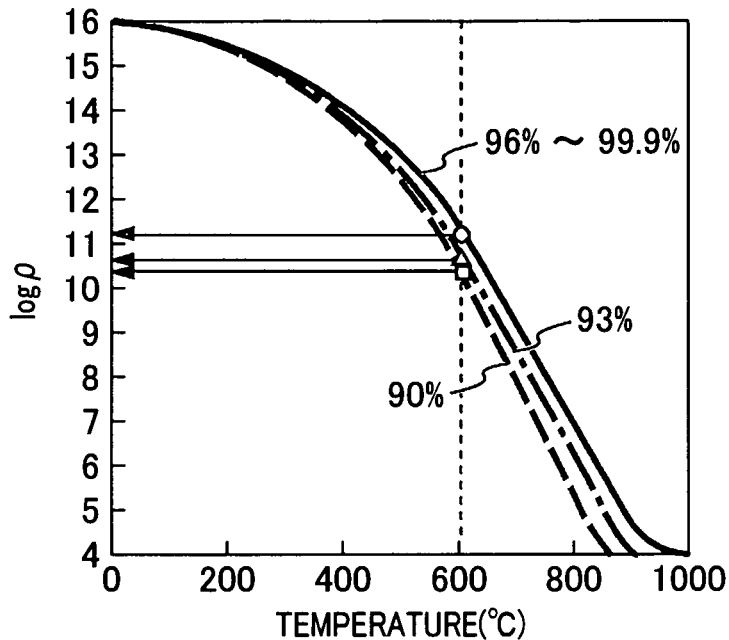
FIG. 8A is a characteristics diagram showing changes of volume resistivity of alumina.

FIG. 8A is a characteristics chart showing temperature characteristics of volume resistivity of a representative alumina. FIG. 8B is a characteristics diagram of changes in direct current resistance $R_{AL}$ between the first plate conductor 130 and the second plate conductor 140 when the thickness d of the dielectric layer 150 is changed.

As shown in FIG. 8A, the volume resistivity p of alumina at 600° C. has a difference of about $4\times10^{10}$ Ωm to $1.4\times10^{11}$ Ωm depending on alumina content.

Figure 8B:
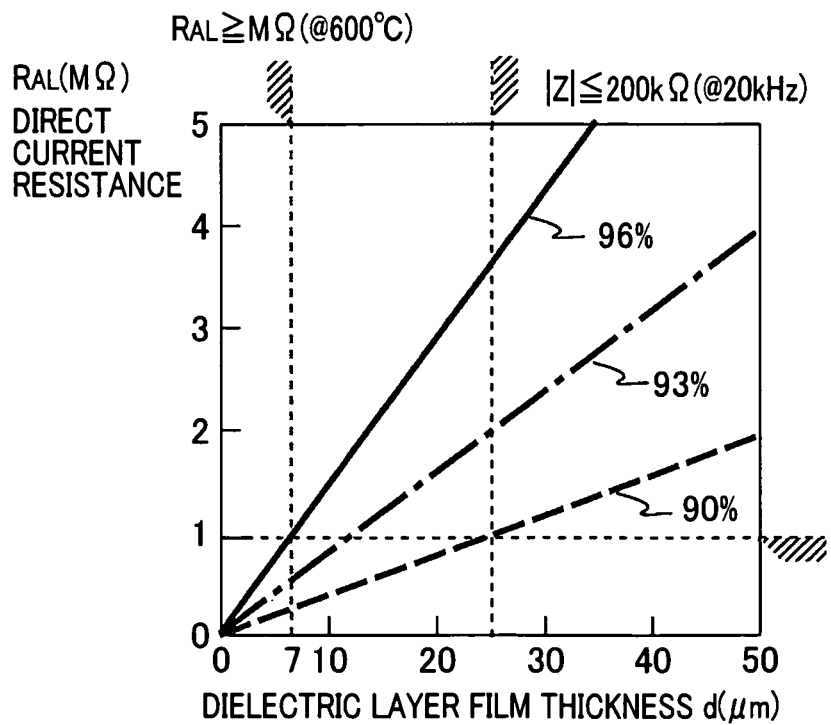
FIG. 8B is a characteristics diagram showing a correlation between the thickness of the dielectric layer using alumina and direct current resistance.

As shown in FIG. 8B, for example, in an instance in which 96 mass percent alumina is used, when the thickness d of the dielectric layer 150 is 7 μm or more, the direct current resistance $R_{AL}$ of 1 MΩ or more is ensured even at 600° C.

Therefore, for example, in an instance in which 96 mass percent alumina is used, when the dielectric layer 150 is set to 7 μm or more and 25 μm or less, the alternating current impedance becomes 200 kΩ or less. A direct current resistance of 1 MΩ or more at 600° C. can be ensured. As a result of the direct current resistance being 1 MΩ or more, insulating properties of the capacitance component 13 can be ensured. Direct current does not flow from the direct-current power source 21 to the capacitance component 13. Direct current detection accuracy of the direct-current detector 23 is improved. Therefore, disconnection detection is expected to be facilitated without PM detection being affected.

The results of a test conducted to confirm the effects regarding detection of disconnection abnormality occurring within the particulate matter detection element 10 of the present embodiment will be described with reference to FIG. 9A and FIG. 9B.

Figure 9A:
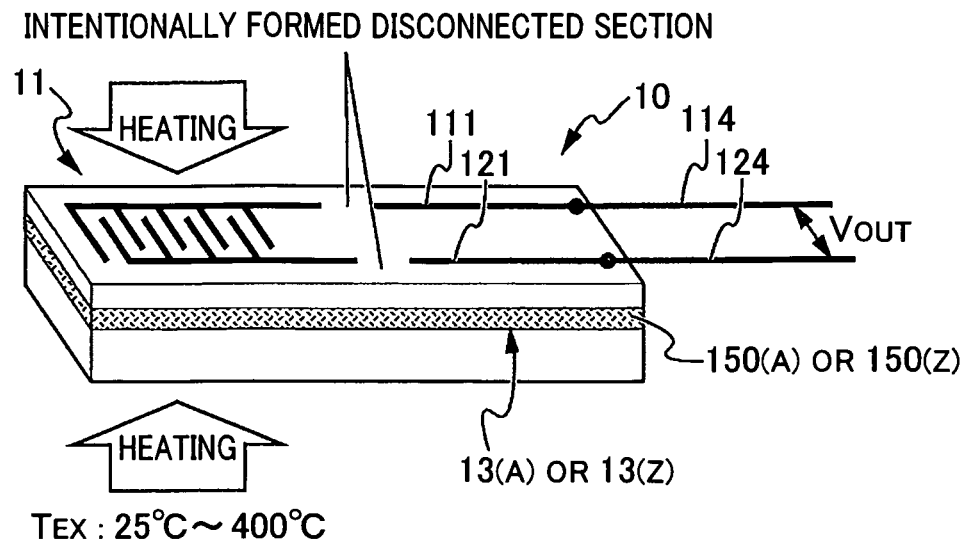
FIG. 9A is a perspective view of a method of a second test conducted to confirm the effects of the present invention.

As shown in FIG. 9A, as dielectric layers $150_{(A)}$ and $150_{(Z)}$ respectively configuring capacitance components $13_{(A)}$ and $13_{(Z)}$, particulate matter detection elements $10_{(A)}$ and $10(Z)$ respectively using alumina and zirconia were made. Furthermore, a sample intentionally simulating disconnection within the particulate matter detection element was made by the detection lead sections 111 and 121 being disconnected. The changes in output detected by the alternating-current detector 24 when measurement temperature $T_{EX}$ is heated from room temperature to 400° C. at which the particulate matter detection element is ordinarily used were examined. The results of the examination are shown in FIG. 9B.

Figure 9B:
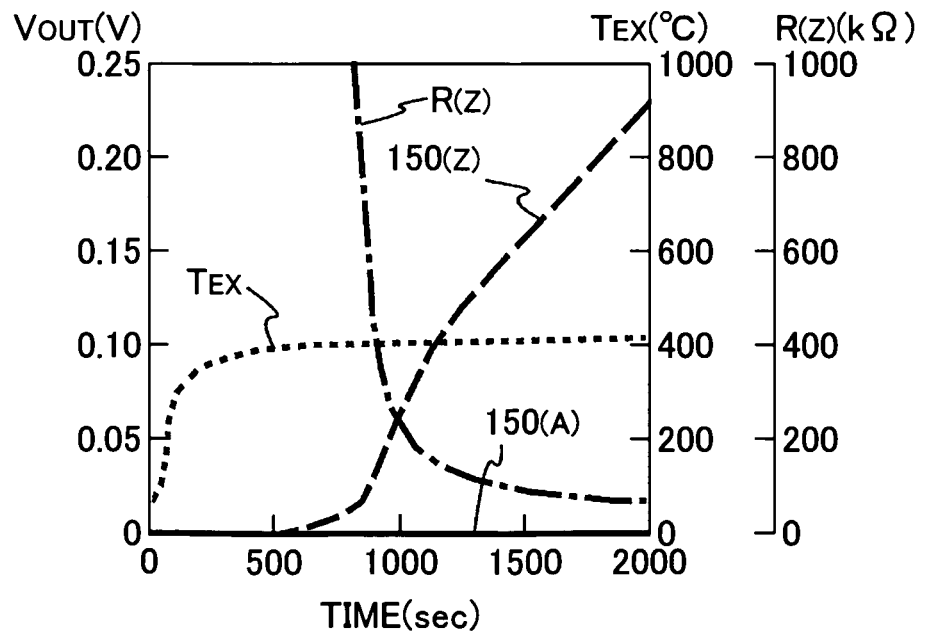
FIG. 9B is a characteristics diagram showing the effects of the present invention with a comparative example.

As indicated by $150_{(A)}$ in FIG. 9B, when alumina is used, no alternating current is detected even when the measurement temperature rises to 400° C. The disconnected state can be detected.

On the other hand, as indicated by $150_{(Z)}$ in FIG. 9B, when zirconia is used, direct current resistance $R_{(Z)}$ between the plate conductors 130 and 140 gradually decreases with the increase in measurement temperature. The output voltage gradually increases when 500 seconds have elapsed from the start of measurement.

This is assumed have occurred because conductivity is generated in accompaniment with temperature increase as a result of the semiconductor properties of zirconia.

Therefore, at temperatures near 400° C. that is the usage environment, zirconia, in which the alternating current impedance is low, detection is difficult, and sufficient insulation cannot be ensured, and therefore it has been found to be unsuitable for use in the dielectric layer 150 of the particulate matter detection element 10 of the present embodiment.

On the other hand, alumina actualizes sufficient insulation and alternating current impedance facilitating detection when the thickness d of the dielectric layer 150 is formed to be 7 μm or more and 25 μm or less. Therefore, alumina has been found to be effective as the dielectric layer 150 of the particulate matter detection element 10 of the present embodiment.

As insulating ceramic materials other than alumina as the material for the dielectric layer 150, any material selected from beryllia, calcia, magnesia, thoria, and spinel, or a composite ceramic composed of these materials are expected to be favorably used.

A material preferably meets the following conditions when used as the material for the dielectric layer 150 of the particulate matter detection element 10 of the present embodiment.

In other words, the material has a predetermined volume resistivity by which the direct current resistance of the dielectric layer 150 becomes 1 MΩ or more at 600° C. The area S of the plate conductors 130 and 140 and the thickness d of the dielectric layer 150 are set such that the alternating current impedance of the dielectric layer 150 becomes 200 kΩ or less, and the direct current resistance of the dielectric layer 150 at 600° C. becomes 1 MΩ or more.

The relationship of $C_{13} = \in_r \cdot \in_0 \cdot S/d$ is established among the relative permittivity $\in_r$ of the insulating ceramic configuring the dielectric layer 150, the vacuum permittivity $\in_0$, the thickness d of the dielectric layer 150, the area S of the plate conductors 130 and 140, and the capacitance $C_{13}$ of the capacitance component 13. The relationship $Z = 1/(j \cdot \omega \cdot C_{13}) = 1/(j \cdot 2\pi \cdot f \cdot C_{13})$ (j being an imaginary unit), and therefore $|Z| = 1/(2\pi \cdot f \cdot C_{13})$ are established among the alternating current impedance Z, the capacitance $C_{13}$, and the sweeping frequency f.

In addition, the direct current resistance $R_{13}$ of the capacitance component 13 is calculated from the volume resistivity ρ (Ωm) of the insulating ceramic material at 600° C. and the thickness d of the dielectric layer 150. The direct current resistance $R_{13}$ is preferably 1 MΩ or more.

In other words, the volume resistivity ρ or the thickness d of the dielectric layer 150 is set such that $\rho \cdot d \geq 1$ (MΩ)

Second Embodiment

Figure 10:
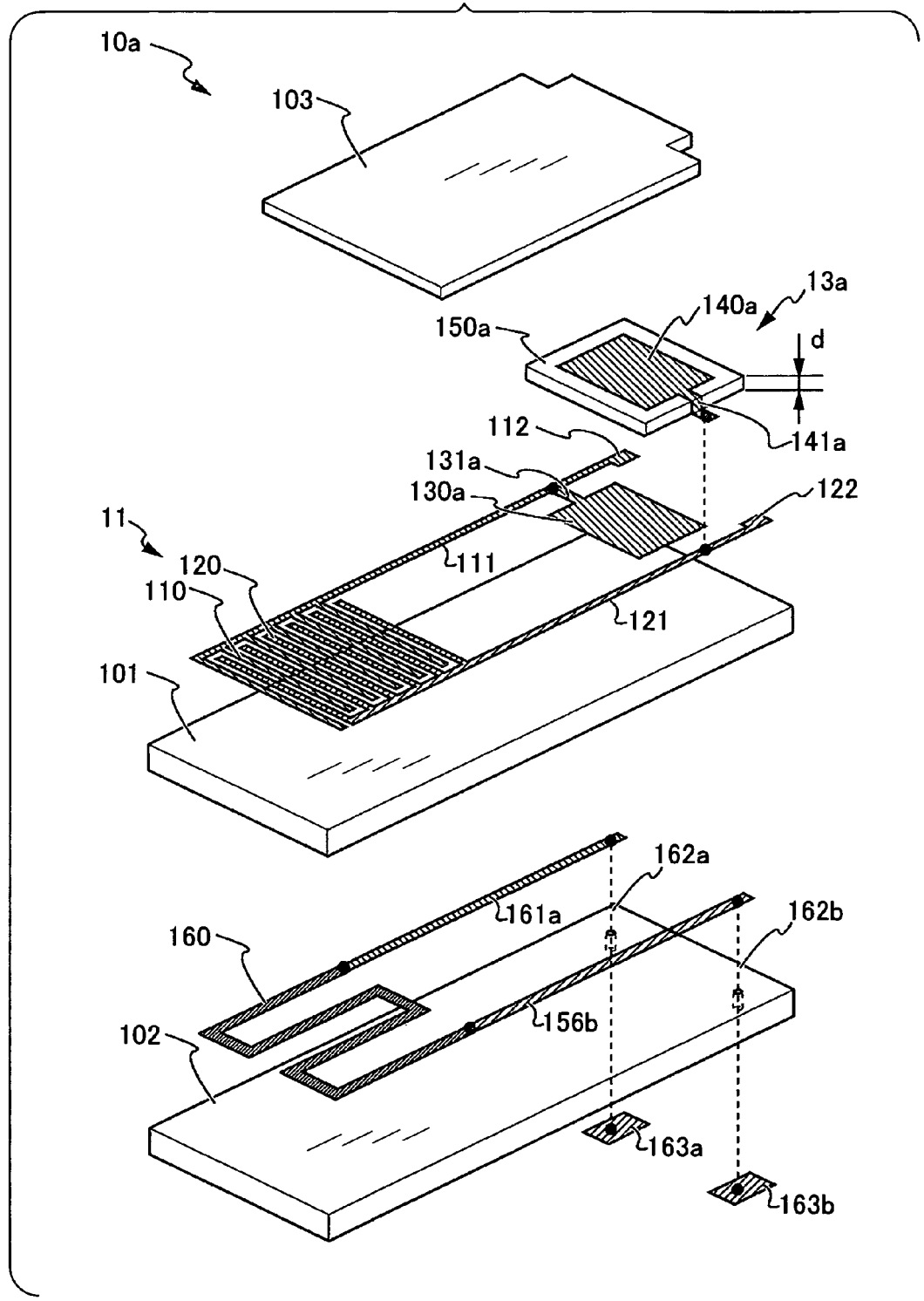
FIG. 10 is an exploded perspective view of an overview of a particulate matter detection element used in a particulate matter detecting device according to a second embodiment of the present invention.

A particulate matter detection element 10a according to a second embodiment of the present embodiment will be described with reference to FIG. 10. In the second embodiment and subsequent embodiments, configurations similar to those according to the first embodiment are given the same reference numbers. Explanations thereof are omitted.

According to the first embodiment, an example is described in which the dielectric layer 150 is formed in a rough plate shape by the doctor blade method or the like. The dielectric layer 150 is layered on the rear-surface side of the insulating substrate 101 configuring the detection section 11. As an alternative, as described according to the second embodiment, a capacitance element may be formed on the front-surface side of the insulating substrate 101 on which the detection electrodes 110 and 120 are provided. Specifically, a first plate conductor 130a and a first conductor lead section 121a may be formed on the front surface of the insulating substrate 101 on which the detection electrodes 110 and 120 are provided. A printing paste using insulating ceramic is made. A dielectric layer 105a is formed by printing such as to cover the first plate conductor 130a. Furthermore, a second plate conductor 140a and a second conductor lead section 141a is formed such as to be layered on the dielectric layer 150a.

As a result of a configuration such as that described above, the first conductor lead section 131a and the detection lead section 11 can be connected, and the second conductor lead section 141a and the detection lead section 121 can be connected directly without the through-hole electrodes 132, 142, and 143 therebetween. Therefore, manufacturing of the particulate matter detection element 10a of the present embodiment is facilitated.

The thickness d of the dielectric layer 150a that can be formed by thick film printing is about several μm to 20 μm. Therefore, a suitable thickness d can be easily formed through adjustment of printing pressure and printing frequency, such that a capacitance component 13a has desired alternating current impedance $Z_{13}$ and direct current resistance $R_{13}$.

Third Embodiment

Figure 11:
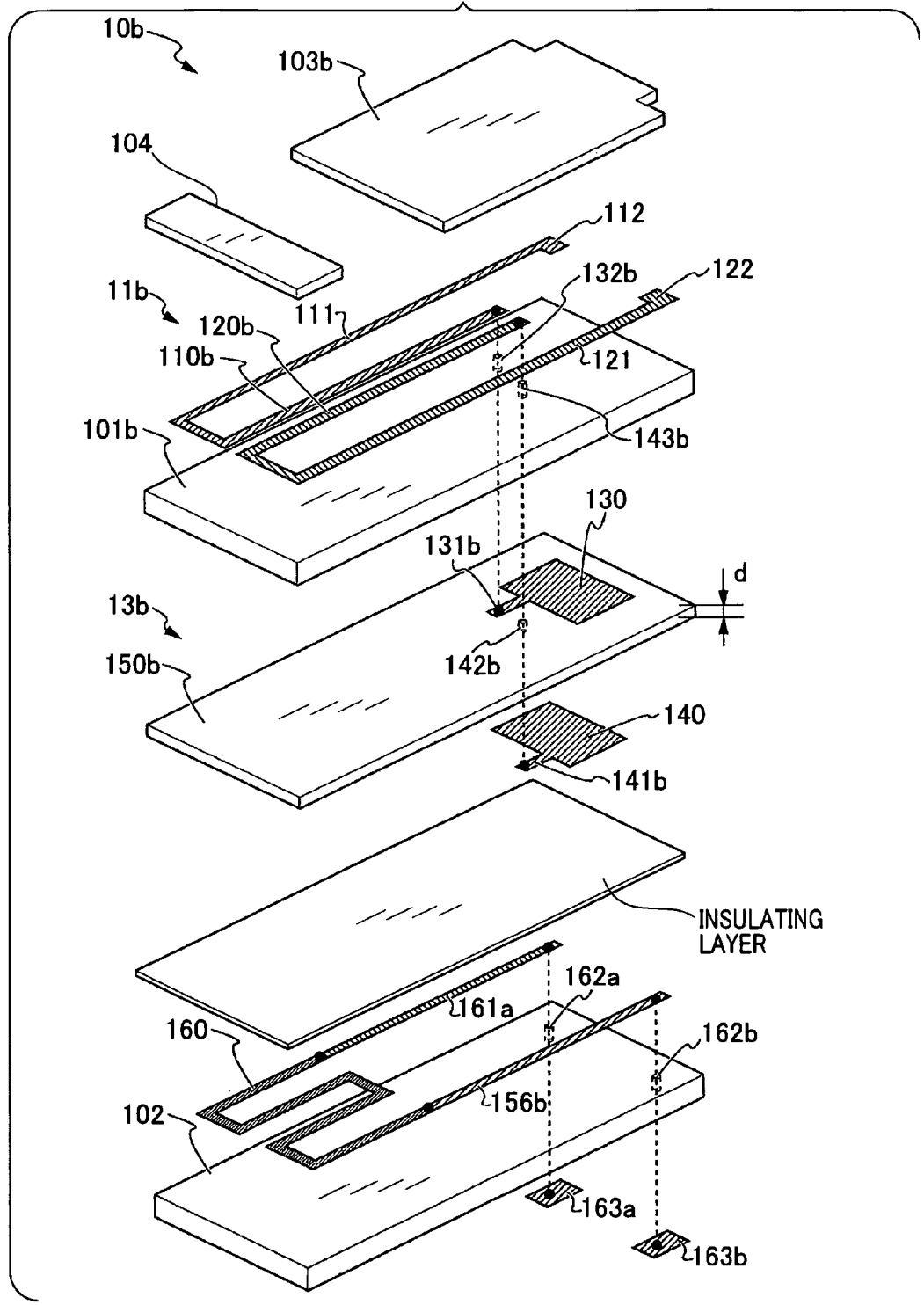
FIG. 11 is an exploded perspective view of an overview of a particulate matter detection element used in a particulate matter detecting device according to a third embodiment of the present invention.

A particulate matter detection element 10b according to a third embodiment of the present embodiment will be described with reference to FIG. 11 and FIG. 12.

According to the first and second embodiments, a configuration is described in which the detection section 11 is a plurality of detection electrodes 110 and 120 opposing each other such as to be arrayed in a comb-shape. As an alternative, as described according to the third embodiment, detection electrodes 110b and 120b that extend linearly may be disposed opposing each other as opposing electrodes. The detection electrodes 110b and 120b may be covered by an insulating protective layer 103b provided with an opening section 104 such that the detection section 11b is exposed.

According to the third embodiment as well, in a state in which the particulate matter is accumulated between the detection electrodes 110b and 120b, a capacitance component 13b is connected in parallel to the detected resistance $R_{SEN}$. In a state in which the particulate matter is not accumulated between the detection electrodes 110b and 120b, the capacitance component 13b is connected in series between the detection electrodes 110 and 120.

The results of a third test conducted to confirm the effects of the particulate matter detection element 10b according to the third embodiment of the present embodiment will be described with reference to FIG. 12A and FIG. 12B. The method of testing is similar to the above-described method of the second test. A particulate matter detection element according to the third embodiment is used.

Figure 12A:
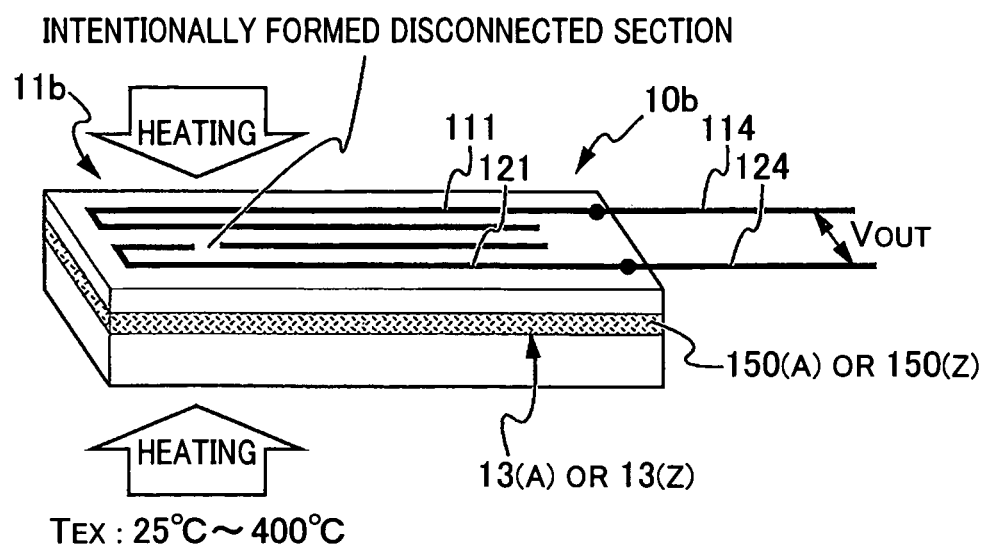
FIG. 12A is a perspective view of a method of a third test conducted to confirm the effects of the present invention.
Figure 12B:
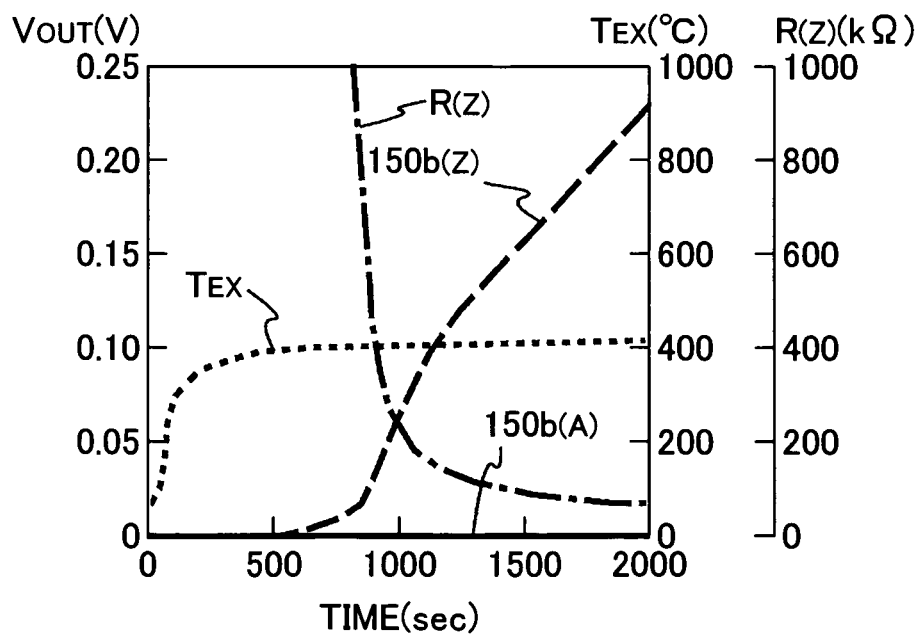
FIG. 12B is a characteristics diagram showing the effects of the present invention with a comparative example.

As shown in FIG. 12A, according to the third embodiment of the present embodiment as well, the test was conducted with an intentional disconnection formed within the particulate matter detection element 10b. As a result, in a manner similar to that according to the first embodiment, as indicated by 150$b_{(A)}$ in FIG. 12B, in an instance in which alumina is used as a dielectric layer 150$b_{(A)}$ configuring a capacitance component 13$b_{(A)}$, disconnection within the detection section 11b can be detected with certainty. On the other hand, as indicated by 150$B_{(Z)}$ in FIG. 12B, in an instance in which zirconia is used as a dielectric layer 150$b_{(Z)}$ configuring a capacitance component 13$b_{(A)}$, insulation resistance $R_Z$ of the dielectric layer 150$b_{(Z)}$ decreases in accompaniment with the increase in temperature $T_{EX}$. Disconnection can no longer be detected.

Therefore, in the particulate matter detection element 10b according to the third embodiment as well, through use of alumina or the like having a predetermined volume resistivity by which the direct current resistance of the dielectric layer 150$b_{(A)}$ at 600° C. becomes 1 MΩ or more, the area S of the parallel plate conductors 130 and 140, and the thickness d of the dielectric layer 150$b_{(A)}$ are set such that the alternating current impedance of the dielectric layer 150$b_{(A)}$ becomes 200 kΩ or less, and the direct current resistance of the dielectric layer 150$b_{(A)}$ at 600° C. becomes 1 MΩ or more. As a result, disconnection abnormality is confirmed to be detected with certainty.

What is claimed is:

1. A detecting device that detects an amount of particulate matter included in a gas to be measured, the detecting device comprising:
    a detection section having a pair of detection electrodes, the detection electrodes formed on a surface of an insulating substrate to oppose each other with space therebetween, the particulate matter accumulated between the detection electrodes forming an electrical resistance to be detected;
    a capacitance component having a dielectric layer and a pair of plate conductors formed on opposite sides of the dielectric layer to oppose each other with the dielectric layer therebetween, the dielectric layer being formed from insulating ceramic, the capacitance component being electrically connected in parallel with the detection electrodes such that a voltage is between the pair of detection electrodes and between the pair of plate conductors;
    a detection circuit having an alternating-current power source that supplies an alternating current to a detection element having the detection electrodes and the capacitance component and an alternating-current detector that detects the alternating current flowing through the detection element.

2. The detecting device according to claim 1, wherein:
    the detection electrodes are formed on an insulation substrate; and
    the capacitance component is layered on integrally with the insulating substrate.

3. The detecting device according to claim 1, wherein the capacitance component is serially connected between the pair of electrodes in a state where there is no conduction pathway by particulate matter accumulated between the pair of detection electrodes.

4. The detecting device according to claim 1, wherein the detection circuit further comprises:
    a direct-current power source supplying a direct current to the detection element; and
    a direct-current detector detecting the direct current flowing through the detection element depending on the amount of the accumulated particulate matter.

5. The detecting device according to claim 1, wherein the capacitance component has an alternating current impedance of 200 kΩ or less and a direct current resistance of 1 MΩ or more measured at a temperature of 600° C. of the capacitance component.

6. The detecting device according to claim 1, the capacitance component is disposed at a position, the position being a temperature of 500° C. or below.

7. The detecting device according to claim 1, wherein:
    one of the plate conductors of the capacitance component is connected to one of the detection electrodes through a lead section; and
    the other of the plate conductors is connected to the other of the detection electrodes through another lead section, thereby the capacitance component is electrically connected in parallel with the detection electrodes.

8. The detecting device according to claim 4, wherein
    the detection element and the detection circuit are connected to each other via a pair of signal lines, the direct current and the alternating current are transmitted via the signal lines between the detection element and the detection circuit.

9. A method for manufacturing a device that detects an amount of particulate matter included in a gas to be measured, the method comprising of steps:
    forming a pair of detection electrodes on a surface of an insulating substrate to oppose each other with space therebetween, the detection electrodes being for detecting the amount of particulate matter; and
    forming a capacitance component having a dielectric layer and a pair of plate conductors formed on opposite sides of the dielectric layer to oppose each other with the dielectric layer therebetween,
    forming lead lines for electrically connecting between the capacitance component and the detection electrodes in parallel with each other such that voltage is applied between the pair of detection electrodes and between the pair of plate conductors;
    wherein the forming step comprises:
    a step of forming the dielectric layer, in which insulating ceramic powder having a predetermined relative permittivity and a predetermined volume resistivity, a predetermined dispersion medium, a predetermined binder, and a predetermined plasticizer are mixed and dispersed into a slurry state or a paste state, the ceramic slurry or the ceramic paste is used to form the dielectric layer such as to be layered on the insulating substrate, by coating or printing;
    a step of forming one of the plate conductors on one of the side surfaces of the dielectric layer;
    a step of forming the other of the plate conductors on the other of the side surfaces of the dielectric layer so that the dielectric layer is sandwiched by the pair of conductors.

* * * * *

UNITED STATES PATENT AND TRADEMARK OFFICE
CERTIFICATE OF CORRECTION

| | | |
|---|---|---|
| PATENT NO. | : 8,860,439 B2 | Page 1 of 1 |
| APPLICATION NO. | : 13/283885 | |
| DATED | : October 14, 2014 | |
| INVENTOR(S) | : Kimata et al. | |

It is certified that error appears in the above-identified patent and that said Letters Patent is hereby corrected as shown below:

In the Claims,

At col. 15, beginning at line 53, should read,

2. The detecting device according to claim 1, wherein:

the detection electrodes are formed on an insulation substrate; and the capacitance component is layered on the insulating substrate.

Signed and Sealed this
Third Day of March, 2015

Michelle K. Lee
*Deputy Director of the United States Patent and Trademark Office*